(12) United States Patent
Teshima et al.

(10) Patent No.: US 9,073,953 B2
(45) Date of Patent: Jul. 7, 2015

(54) METHOD FOR REFINING TRIMETHYLSILANE

(71) Applicant: Central Glass Company, Limited, Ube-shi, Yamaguchi (JP)

(72) Inventors: Takuya Teshima, Sanyoonoda (JP); Takaaki Shibayama, Ube (JP); Yosuke Nakamura, Saitama (JP); Tomoyuki Hiraoka, Ube (JP)

(73) Assignee: Central Glass Company, Limted, Ube-shi (JP)

( * ) Notice: Subject to any disclaimer, the term of this patent is extended or adjusted under 35 U.S.C. 154(b) by 0 days.

(21) Appl. No.: 14/380,079

(22) PCT Filed: Jan. 16, 2013

(86) PCT No.: PCT/JP2013/050639
§ 371 (c)(1),
(2) Date: Jan. 2, 2015

(87) PCT Pub. No.: WO2013/125262
PCT Pub. Date: Aug. 29, 2013

(65) Prior Publication Data
US 2015/0119596 A1    Apr. 30, 2015

(30) Foreign Application Priority Data

Feb. 21, 2012 (JP) ................. 2012-034668

(51) Int. Cl.
*C07F 7/08* (2006.01)
*C07F 7/20* (2006.01)

(52) U.S. Cl.
CPC ............... *C07F 7/20* (2013.01); *C07F 7/0896* (2013.01)

(58) Field of Classification Search
USPC ........................................ 556/451, 453, 456
See application file for complete search history.

(56) References Cited

U.S. PATENT DOCUMENTS

| | | | |
|---|---|---|---|
| 4,824,657 | A | 4/1989 | Jadhav |
| 6,444,013 | B1 | 9/2002 | Helly et al. |
| 7,355,060 | B2 | 4/2008 | Ogawa et al. |
| 2007/0149798 | A1 | 6/2007 | Ogawa et al. |

FOREIGN PATENT DOCUMENTS

| | | | | |
|---|---|---|---|---|
| JP | 2-221110 | A | | 9/1990 |
| JP | 2002-179689 | A | | 6/2002 |
| JP | 2004-115388 | A | | 4/2004 |
| JP | 2005-154336 | A | | 6/2005 |
| JP | 2006-117559 | | * | 5/2006 ............... C07F 7/08 |
| JP | 2006-117559 | A | | 5/2006 |
| JP | 2006-206444 | A | | 8/2006 |

OTHER PUBLICATIONS

Steward et al. "The Effect of Polar Substituents on the Alkali-catalyzed Hydrolysis of Triorganosilanes" J. Am. Chem. Soc., Sep. 23, 1960, pp. 1916-1921, vol. 83, Contribution from the Dow Corning Corporation; Midland, Mich.
International Search Report (PCT/ISA/210) dated Apr. 16, 2013 with English translation (four pages).
Japanese-language Written Opinion (PCT/ISA/237) dated Apr. 16, 2013 (three pages).

* cited by examiner

*Primary Examiner* — Sudhakar Katakam
*Assistant Examiner* — Pancham Bakshi
(74) *Attorney, Agent, or Firm* — Crowell & Moring LLP

(57) ABSTRACT

Disclosed is a method for refining trimethylsilane, including the steps of (1) preparing an activated carbon loaded with at least copper (II) oxide and zinc oxide; (2) adsorbing a trimethylsilane onto the activated carbon; and (3) bringing a trimethylsilane containing silane, methylsilane or dimethylsilane as an impurity into contact with the activated carbon finished with the step (2) to remove the impurity from the trimethylsilane by adsorbing the impurity. According to this method, heat generation of the activated carbon is suppressed and impurities such as dimethylsilane, etc. can be removed efficiently.

8 Claims, No Drawings

METHOD FOR REFINING TRIMETHYLSILANE

TECHNICAL FIELD

The present invention relates to a method for refining trimethylsilane useful as a film-forming raw material for semiconductor production.

BACKGROUND OF THE INVENTION

In recent years, use of trimethylsilane (($CH_3$)$_3$SiH) has been extending as an interlayer insulating film and a film-forming raw material in the field of semiconductors.

As a method of producing trimethylsilane, it is general to use a suitable hydrogenation agent for reduction of trimethylchlorosilane (($CH_3$)$_3$SiCl).

For example, a synthesis method that trimethylchlorosilane and lithium aluminum hydride ($LiAlH_4$) are reacted in a solvent of dimethoxyethane (DME) has been disclosed (Non-patent Publication 1). Furthermore, a method that lithium hydride (LiH) (Patent Publication 1) or diethylaluminum hydride (($C_2H_5$)$_2$AlH) (Patent Publication 2) is used as a hydrogenation agent and a method that lithium aluminum hydride is used as a hydrogenation agent and an aromatic hydrocarbon series organic solvent is used as a solvent have been disclosed (Patent Publication 3).

Trimethylchlorosilane as a common raw material in these synthesis methods is contaminated usually with dozens to thousands ppm of methyltrichlorosilane ($CH_3SiCl_3$), dimethyldichlorosilane (($CH_3$)$_2SiCl_2$), silicon tetrachloride ($SiCl_4$), etc. as impurities. When these impurities react with the hydrogenation agent, the corresponding silanes, that is, methylsilane ($CH_3SiH_3$), dimethylsilane (($CH_3$)$_2SiH_2$) or silane ($SiH_4$) is produced. Furthermore, even in the case of not containing these chlorosilane series impurities at all, there occurs a disproportionate reaction in the process of the reaction with the hydrogenation agent. As a result, trimethylsilane is contaminated with these silanes as impurities. Alternatively, remains of the unreacted chlorosilane series impurities and impurities produced as by-products are also found.

Recently, there has been a demand for very high purity film forming raw materials in the semiconductor production. Using a synthesized trimethylsilane for semiconductors, the amount of these impurities must be reduced.

As a method of removing these impurities, distillation operation is usually used for refining. Besides, recrystallization, reprecipitation and sublimation can be used. Furthermore, there has been disclosed a method of utilizing activated carbon (Patent Publication 4) and a method of washing the gas with an absorbing solution (Patent Publication 5).

In the case of using distillation means, which is the most common, it was necessary to provide a distillation column having a high number of stages to completely remove dimethylsilane having a boiling point comparatively close to that of trimethylsilane, thereby causing a problem of not being economical. Furthermore, when trying to completely remove small amounts of the impurities having close boiling points by distillation, the loss of the product increases. This also leads to the yield reduction.

In contrast with this, it became possible to effectively remove the impurities by the above-mentioned method described in Patent Publication 4 utilizing activated carbon.

PRIOR ART REFERENCES

Patent Publications

Patent Publication1: Japanese Patent Application Publication H2-221110

Patent Publication2: Japanese Patent Application Publication 2004-115388

Patent Publication3: Japanese Patent Application Publication 2005-154336

Patent Publication4: Japanese Patent Application Publication 2006-117559

Patent Publication5: Japanese Patent Application Publication 2006-206444

Non-Patent Publication

Non-patent Publication: J. Amer. Chem. Soc., 83, 1916 (1961)

SUMMARY OF THE INVENTION

In conventional methods using activated carbon, when trimethylsilane to be refined is brought into contact with activated carbon to remove impurities, the activated carbon will have a high temperature by heat of adsorption. Due to this heat, there occurs a mechanical trouble of facilities packed with the activated carbon, adsorbed impurities are desorbed, and there occurs disproportionation reaction of trimethylsilane. As a result, problems such as the concentration of the impurities in the substance to be refined becoming high, etc. may be caused.

This is because not only the impurities but also trimethylsilane to be refined is adsorbed onto the activated carbon, thereby generating heat of adsorption. The activated carbon has a porous structure and works as a heat insulator by itself. Therefore, heat generated in a packed tower packed with the activated carbon tends to be accumulated. Furthermore, besides heat of adsorption, heat of reaction by the disproportionation reaction which is caused by heat of adsorption further increases the temperature of the activated carbon in the packed tower.

In a refining method to remove the impurities such as dimethylsilane, etc. from trimethylsilane by using activated carbon, the aim of the present invention is to provide a method for refining trimethylsilane, which is capable of efficiently removing the impurities by suppressing heat generation of the activated carbon.

As a result of intensive studies made by the present inventors to achieve the above aim, we have discovered that it is possible to suppress heat generation of the activated carbon by previously adsorbing a trimethylsilane onto an activated carbon containing copper (II) oxide and zinc oxide and then bringing a trimethylsilane containing impurities into contact with this activated carbon, thereby efficiently removing impurities, such as dimethylsilane, etc., and then have reached the present invention.

That is, the present invention provides a method for refining trimethylsilane, comprising the steps of (1) preparing an activated carbon loaded with at least copper (II) oxide and zinc oxide; (2) adsorbing a trimethylsilane onto the activated carbon; and (3) bringing a trimethylsilane comprising silane, methylsilane or dimethylsilane as an impurity into contact with the activated carbon finished with the step (2) to remove the impurity from the trimethylsilane by adsorbing the impurity.

Furthermore, it provides the above-mentioned method for refining trimethylsilane, which is characterized by that, in the step (2), the trimethylsilane is adsorbed onto the activated carbon by bringing a diluted trimethylsilane into contact with the activated carbon.

Effects of the Invention

According to the method of the present invention, when silane, methylsilane and dimethylsilane in trimethylsilane are adsorbed and removed by using the activated carbon loaded with at least copper (II) oxide and zinc oxide, it is possible to suppress heat produced by the activated carbon. Therefore, it is possible to reduce the impurities to less than 1 volume ppm as the lower limit of determination.

DETAILED DESCRIPTION

The present invention is described below in more detail.

Trimethylsilane as the refining target contains silane, methylsilane or dimethylsilane, and it is obtained by the above-mentioned well-known method in which trimethylchlorosilane (($CH_3$)$_3$SiCl) is reduced by a hydrogenation agent.

(1) about a Step for Preparing the Activated Carbon Loaded with Copper (II) Oxide and Zinc Oxide If the activated carbon used for the step is, what is called, the loaded activated carbon containing copper (II) oxide and zinc oxide, any forms of powdered forms, grained forms, sheet forms, crushed forms, granulated forms and fibre forms can be used. These activated carbons can be bought as goods on the market. When it is used as a packed tower, grained forms, crushed forms and granulated forms, etc. are usable preferably.

In general, the loaded activated carbon is accelerated in chemical adsorption by not only physical adsorption but also a chemical interaction between a substance to be loaded and a substance to be adsorbed. For this reason, a method in which copper (II) oxide and zinc oxide are loaded onto the activated carbon may be any method, as long as it is a method in which this chemical interaction can be expected.

For example, there are a method in which raw materials which were crushed before carbonization during producing the activated carbon are mixed with powders of copper (II) oxide and zinc oxide, followed by carbonization and activation, a method of loading onto a ready-made activated carbon using surface potential, and a method in which powdered carbon and copper (II) oxide and zinc oxide are kneaded in the presence of an appropriate binder, followed by granulation and then a heat treatment to conduct the loading. Materials which can be hardened after kneading can be used as a binder. Specifically, it is possible to use inorganic substances used as inorganic adhesives, such as cement, water glass, solder, etc., and synthetic resins, such as thermosetting resins, thermoplastic resins, etc. For example, a phenol resin, an epoxy resin, an unsaturated polyester resin, an alkyd resin, a melamine resin, a urea resin, polyurethane and thermosetting polyimide can be used as a thermosetting resin. Polyethylene, polypropylene, polyvinyl chloride, an acrylic resin, polyvinyl chloride, polystyrene, polyvinyl acetate, polytetrafluoroethylene, an ABS resin, an AS resin, polyamide, polycarbonate, cyclic polyolefin, etc. can be used as a thermoplastic resin.

As to the concentrations of copper (II) oxide and zinc oxide relative to the activated carbon, the content of 1-10 weight % as Cu and the content of 1-10 weight % as Zn are preferable, and the ratio of copper (II) oxide to zinc oxide is not particularly limited. In case that the concentrations of copper (II) oxide and zinc oxide as Cu and Zn are less than 1 weight %, the ability to remove silane, methylsilane and dimethylsilane become low, thereby making a complete removal impossible. In addition, if the concentrations of copper (II) oxide and zinc oxide as Cu and Zn are more than 10 weight %, it is not preferable because the adsorption capacity of the activated carbon itself becomes extremely low with lowering of the specific surface area.

(2) Regarding a Step in which Trimethylsilane is Adsorbed onto the Above Activated Carbon In the step, trimethylsilane is adsorbed onto the activated carbon which was prepared in the above step (1). It is preferable that the trimethylsilane used for this adsorption has a purity as high as possible. It is preferable to use a trimethylsilane having a purity of at least 95% or greater, more preferably 99.9% or greater. With regard to impurities included therein, silane, methylsilane and dimethylsilane may be included. However, corrosive substances such as trimethylchlorosilane have a possibility of not only causing a damage to the facility to demonstrate the present invention but also causing a contamination of a gas to be gained by the method for refining of the present invention. Therefore, it is preferable that the content is less than 1 volume %.

Furthermore, as the adsorption method, trimethylsilane can be adsorbed by a contact with the activated carbon. In this method, there is a method in which trimethylsilane in the form of gas or liquid is brought into contact with the activated carbon. A method of making the contact in the form of gas with a large diffusion coefficient is efficient. Furthermore, either batch type or flow type can be used. For industrially improving the production efficiency, it is preferable to use flow type.

It is preferable that the temperature of the activated carbon at the time of adsorption is as low as possible, considering disproportionation reaction of trimethylsilane. Since the boiling point of trimethylsilane is 6.7° C., in case of being brought into contact in the form of gas under atmospheric pressure, around room temperature (10-40° C.) is preferable. When the temperature of the activated carbon is more than 100° C. to make the contact, the disproportionation reaction of trimethylsilane occurs easily. Therefore, the possibility of by-production of impurities such as tetramethylsilane (($CH_3$)$_4$Si), etc. becomes higher. In particular the disproportionation reaction becomes conspicuous at more than 135° C. Tetramethylsilane produced as a byproduct is adsorbed and remains on the activated carbon. After that, when impurity-containing trimethylsilane as the refining target is brought into contact, there is a risk of contamination of the substance to be refined.

In the present step, an effect of the present invention can be obtained as long as trimethylsilane is adsorbed onto the activated carbon. Therefore, it is only necessary to adsorb a desired amount of trimethylsilane. For example, considering increase of the temperature of the activated carbon by adsorbing trimethylsilane onto the activated carbon, it is preferable to finish the present step when the temperature of the activated carbon at the time of adsorption is less than 100° C. Furthermore, it is more preferable to finish the present step by conducting the adsorption until the temperature increase upon adsorption stops.

Furthermore, in case of bringing trimethylsilane into contact with the activated carbon, considering raw materials cost and simplification of the steps, it is preferable to bring only trimethylsilane into the contact. In this case, however, in cooling to adjust the temperature of the activated carbon to a temperature at which the disproportionation reaction hardly occurs, there are risks, such as load of the cooling ability becoming large and a facility structure of a tower of the activated carbon becoming complicated. One of countermeasures to solve these problems, it is preferable to bring trimethylsilane of a low temperature into contact. There is, however, a limit of an effect on reducing the load because the boiling point of trimethylsilane is 6.7° C. Therefore, it is preferable to dilute trimethylsilane with a gas which is inactive against trimethylsilane and hard to be adsorbed onto the activated carbon, and then make a contact with the activated carbon.

In this case, as a gas used for the dilution, it is possible to cite rare gases, such as helium, neon, argon, krypton, xenon, etc. and nitrogen. A gas which is highly reactive with trimethylsilane is not preferable, because other impurities are produced and have an effect on the purity. Furthermore, a gas which is highly reactive with or easily adsorbed onto the activated carbon, is not preferable, due to the possibility to cause lowering of the adsorption capability.

Furthermore, a dilution ratio at the time of dilution is not especially limited. The aim of the present step is to suppress the temperature increase of the activated carbon and to adsorb trimethylsilane. Thus, it is preferable to conduct the adsorption at a temperature of the activated carbon during the present step so that the disproportionation reaction caused by heat of adsorption of trimethylsilane is not generated. Thus, the dilution ratio can be properly selected depending on the supply rate per hour of the gas made into the contact and the temperature of the activated carbon upon the contact. In general, as trimethylsilane of a higher concentration is adsorbed, there is observed a sharp temperature increase by heat of adsorption. In order to avoid this, it is preferable to conduct the adsorption with dilution.

The dilution ratio at the time of dilution as the volume ratio of the inert gas to trimethylsilane is preferably 0.5-100 times. If the dilution ratio is over 100 times, considering the time for the adsorption and the amount of the gas which is used for dilution, it takes a long time, thereby lowering the treatment efficiency. In case that the dilution ratio is less than 0.5 times, it is difficult to obtain an effect by dilution.

Also, it is not necessary to make the dilution ratio of trimethylsilane in the present step constant. At the initial stage of the present step, a large amount of heat of adsorption tends to be generated. Therefore, it is preferable to conduct the adsorption with a relatively high dilution ratio.

Furthermore, before adsorbing trimethylsilane onto the activated carbon in the present step, it is preferable to conduct a heat treatment of the activated carbon. This heat treatment is a treatment to remove adsorbed water, etc. by heating the activated carbon at 100-300° C. and vacuum degassing or inert gas flow.

(3) Regarding the Step of Bringing a Trimethylsilane Containing the Impurities into Contact with the Activated Carbon Finished with the Above-Mentioned Step (2)

In the present step, trimethylsilane as a refining target containing silane, methylsilane or dimethylsilane as an impurity is brought into contact with the activated carbon finished with the above-mentioned step (2). As the contact method, there are a method to bring into contact by gas and a method to bring into contact by liquid. It is more efficient to bring into contact by gas having a large diffusion coefficient. Furthermore, either batch type or flow type can be used. To remove the impurities efficiently, flow type is preferable. Even among them, one with a multistage is superior and more preferable.

The temperature of the activated carbon upon the contact is the same as that of the above-mentioned step (2).

By bringing an impurity-containing trimethylsilane as the refining target into contact with the activated carbon finished with the above-mentioned step (2), it is considered that the impurities are replaced with the trimethylsilane adsorbed by the above-mentioned step (2) or are adsorbed onto the activated carbon's surface onto which trimethylsilane is not adsorbed, thereby removing the impurities. Furthermore, since adsorption of trimethylsilane onto the activated carbon has already been conducted by the above-mentioned step (2), an abrupt adsorption of trimethylsilane itself to be refined is blocked. Thus, as compared with the case of not conducting the above-mentioned step (2), heat generation of the activated carbon is suppressed, and the production of impurities caused by heating is also suppressed.

Thus, as a result of the possibility of blocking an abrupt adsorption of trimethylsilane as the refining target, heat generation of the activated carbon by heat of adsorption is suppressed. With this, the disproportionation reaction of trimethylsilane is suppressed, and then the increase of the impurity concentration can be suppressed. Accordingly, it becomes possible to obtain trimethylsilane of high purity.

In the following, the present invention is specifically explained based on examples, but the present invention is not limited to the following Examples.

EXAMPLES

Examples 1-5

A packing material in a packed tower, in which 30 kg of an activated carbon (GRANULAR SHIRASAGI XRC 410 made by Japan Enviro Chemicals, Ltd.: content 1-10 weight % as Cu, 1-10 weight % as Zn) including zinc oxide and copper oxide by loading had been packed in a tube made of SUS 304 and having an inner diameter of 158.4 mm and a length of 3350 mm (the packing height of the activated carbon: 3000 mm), was subjected to a vacuum degassing at 200° C. for one hour, thereby detaching water attached to the activated carbon. After this, it was cooled down once to room temperature of 25° C.

After this, trimethylsilane was adsorbed by allowing a mixed gas which was prepared by diluting trimethylsilane with nitrogen gas (both of their purities are more than 99.99%) under a dilution condition shown in Table 1 to flow through the above-mentioned packed tower until the temperature increase caused by heat of adsorption was not observed. The highest temperature in the packed tower is shown in Table 1, which was observed in the packed tower at that time. In each case, the temperature was sufficiently lower than the temperature at which the disproportionation reaction occurs conspicuously.

After adsorbing trimethylsilane, the packed tower was restored to room temperature (25° C.) while purging the packed tower with nitrogen gas for two hours. After this, a trimethylsilane containing 62 volume ppm of methylsilane and 248 volume ppm of dimethylsilane was allowed to flow at 100 sccm to the packed tower under atmospheric pressure to conduct a refinement for the purpose of removing these two impurities. The temperature of the packed tower during the refinement was 33° C. in each Example.

A gas at an outlet of the packed tower at the time of the refinement was analyzed by a gas chromatography and a gas chromatograph mass spectrometry apparatus. The results of analysis are shown in Table 1. As a result, both of methylsilane and dimethylsilane were less than 1 volume ppm as the lower limit of determination. In addition, at the same time, the contents of methane and tetramethylsilane were analyzed in the same way. With this, both of them were less than 1 volume ppm as the lower limit of determination.

TABLE 1

| No. | Example 1 | Example 2 | Example 3 | Example 4 | Example 5 |
|---|---|---|---|---|---|
| Flow rate of $N_2$ (slm) | 6.0 | 9 | 19 | 9.5 | 22.5 |
| Flow rate of trimethylsilane (slm) | 4.0 | 1 | 1 | 0.5 | 0.5 |

TABLE 1-continued

| No. | Example 1 | Example 2 | Example 3 | Example 4 | Example 5 |
|---|---|---|---|---|---|
| Dilution ratio | 1.5 | 9 | 19 | 19 | 45 |
| Maximum temperature of the packed tower at pretreatment (° C.) | 40 | 30 | 26 | 26 | 26 |
| Analysis result of methylsilane and dimethylsilane | <1 vol ppm (less than the lower limit of determination) | <1 vol ppm (less than the lower limit of determination) | <1 vol ppm (less than the lower limit of determination) | <1 vol ppm (less than the lower limit of determination) | <1 vol ppm (less the than lower limit of determination) |

Example 6

A packing material in a packed tower, in which 30 kg of the same activated carbon as that of Example 1 had been packed in a tube made of SUS 304 and having an inner diameter of 158.4 mm and a length of 3350 mm (packing height of the activated carbon: 3000 mm), was subjected to a vacuum degassing at 200° C. for one hour, thereby detaching water attached to the activated carbon. After that, it was cooled down once to room temperature of 25° C.

After that, a mixed gas (dilution ratio is approximately 3.3 times) prepared by a mixing while supplying trimethylsilane (purity is more than 99.9%) at a flow rate of 3 slm and nitrogen gas (purity is more than 99.999%) at a flow rate of 10 slm was allowed to flow. When the total amount of trimethylsilane flow became 20 kg, supply of the mixed gas was stopped. Thus, trimethylsilane was adsorbed. According to a thermometer at the centre of the activated carbon, the temperature of the packed tower was always under 100° C. during supplying the mixed gas.

After stopping the supply, the packed tower was restored to room temperature (25° C.) while purging the packed tower with nitrogen gas for two hours. After that, 30 kg of trimethylsilane containing 10 volume ppm of silane and 500 volume ppm of dimethylsilane was allowed to flow at a flow rate of 17 slm to the packed tower to conduct a refinement for the purpose of removing these two impurities. The temperature of the packed tower during the refinement was 31° C.

A gas at an outlet of the packed tower at the time of the refinement was analyzed by a gas chromatography and a gas chromatograph mass spectrometry apparatus. As a result, both of the concentrations of silane and dimethylsilane were less than 1 volume ppm as the lower limit of determination. In addition, at the same time, the contents of methane and tetramethylsilane were analyzed in the same way. With this, both of them were less than 1 volume ppm as the lower limit of determination.

Example 7

A packing material in a packed tower, in which 62 g (the packed length is 300 mm) of an activated carbon the same as that of Example 1 had been packed in a stainless steel tube having an inner diameter of 22.1 mm and a length of 600 mm, was subjected to a vacuum degassing at 250° C. for one hour. After this, it was restored to room temperature (25° C.). A mixed gas which was prepared by diluting trimethylsilane with nitrogen gas (both of their purities are more than 99.999%) at a dilution ratio of 0.6 times as a volume ratio was allowed to flow at a flow rate of 0.5 slm to flow through the packed tower to adsorb trimethylsilane until the temperature increase caused by heat of adsorption was not observed.

After adsorbing trimethylsilane, the packed tower was restored to room temperature (25° C.) while purging the packed tower with nitrogen gas for two hours. After this, trimethylsilane containing 62 volume ppm of methylsilane and 248 volume ppm of dimethylsilane was allowed to flow at 100 sccm to the packed tower under atmospheric pressure to conduct a refinement for the purpose of removing these two impurities. The temperature of the packed tower during the refinement was 32° C.

A gas at an outlet of the packed tower at the time of the refinement was analyzed by a gas chromatography and a gas chromatograph mass spectrometry apparatus. As a result, the concentrations of methylsilane and dimethylsilane were less than 1 volume ppm as the lower limit of determination. In addition, at the same time, the contents of methane and tetramethylsilane were analyzed in the same way. With this, both of them were less than 1 volume ppm as the lower limit of determination.

Example 8

A packing material in a packed tower, in which 62 g (the packed length is 300 mm) of an activated carbon the same as that of Example 1 had been packed in a stainless steel tube having an inner diameter of 22.1 mm and a length of 600 mm, was subjected to a vacuum degassing at 250° C. for one hour. After this, a mixed gas which was prepared by diluting trimethylsilane with nitrogen gas (both of their purities are more than 99.999%) at a dilution ratio of 50 times as a volume ratio was allowed to flow at a flow rate of 0.5 slm to flow through the packed tower to adsorb trimethylsilane until the temperature increase caused by heat of adsorption was not observed.

After adsorbing trimethylsilane, the packed tower was restored to room temperature (25° C.) while purging the packed tower with nitrogen gas for two hours. After this, trimethylsilane containing 62 volume ppm of methylsilane and 248 volume ppm of dimethylsilane was allowed to flow at 100 sccm under atmospheric pressure to conduct a refinement for the purpose of removing these two impurities. The temperature in the packed tower during the refinement was 29° C.

A gas at an outlet of the packed tower at the time of the refinement was analyzed by a gas chromatography and a gas chromatograph mass spectrometry apparatus. As a result, the concentrations of methylsilane and dimethylsilane were less than 1 volume ppm as the lower limit of determination. In addition, at the same time, the contents of methane and tetramethylsilane were analyzed in the same way. With this, both of them were less than 1 volume ppm as the lower limit of determination.

Comparative Example 1

An operation was conducted in the same way as that of Example 6, except not conducting a treatment of adsorbing trimethylsilane. During this, the temperature of a packed tower rose to 380° C. at the maximum.

A gas at an outlet of the packed tower was analyzed by a gas chromatography and a gas chromatograph mass spectrometry apparatus. As a result, not only 500 volume ppm of dimethylsilane but also 2000 volume ppm of tetramethylsilane and 100 volume ppm of methane were detected. Therefore, it was difficult to conduct a desired refinement. It is considered that this result was obtained because disproportionation reaction was occurred conspicuously by the temperature rise.

Comparative Example 2

An operation was conducted in the same way as that of Example 7 except not conducting a treatment of adsorbing trimethylsilane. During this, the temperature of the packed tower rose to 267° C. at the maximum.

A gas at an outlet of a packed tower was analyzed by a gas chromatography and a gas chromatograph mass spectrometry apparatus. As a result, not only 78 volume ppm of methylsilane and 280 volume ppm of dimethylsilane but also 410 volume ppm of tetramethylsilane and 100 volume ppm of methane were detected. Therefore, it was difficult to conduct a desired refinement. It is considered that this result was obtained because disproportionation reaction was occurred conspicuously by the temperature rise.

INDUSTRIAL APPLICABILITY

The present invention can be used for refining trimethylsilane with an activated carbon. Especially, it becomes an effective method, when the generation of impurities becomes problematic, due to heat of adsorption generated by adsorbing trimethylsilane onto an activated carbon.

The invention claimed is:

1. A method for refining trimethylsilane, comprising the steps of:
(1) preparing an activated carbon loaded with at least copper (II) oxide and zinc oxide;
(2) adsorbing a first trimethylsilane onto the activated carbon; and
(3) bringing a second trimethylsilane comprising silane, methylsilane or dimethylsilane as an impurity into contact with the activated carbon finished with the step (2) to remove the impurity from the second trimethylsilane by adsorbing the impurity onto the activated carbon.

2. The method for refining trimethylsilane according to claim 1, wherein the step (2) is conducted by bringing a diluted trimethylsilane obtained by diluting the first trimethylsilane into contact with the activated carbon.

3. The method for refining trimethylsilane according to claim 1, wherein, in between the steps (1) and (2), while the activated carbon is heated at 100-300° C., the activated carbon is subjected to a vacuum degassing or an inert gas flow.

4. The method for refining trimethylsilane according to claim 1, wherein, in the step (2), the first trimethylsilane has a purity of more than 95%.

5. The method for refining trimethylsilane according to claim 1, wherein the step (2) is finished when temperature of the activated carbon during the step (2) is lower than 100° C.

6. The method for refining trimethylsilane according to claim 1, wherein the step (2) is finished when temperature increase of the activated carbon during the step (2) stops.

7. The method for refining trimethylsilane according to claim 1, wherein the step (2) is conducted by bringing a mixed gas obtained by diluting the first trimethylsilane with an inert gas selected from the group consisting of helium, neon, argon, krypton, xenon and nitrogen into contact with the activated carbon.

8. The method for refining trimethylsilane according to claim 7, wherein, in the step (2), volume of the inert gas is 0.5-100 times that of the first trimethylsilane.

* * * * *